(12) United States Patent
Balamurugan et al.

(10) Patent No.: US 12,728,237 B2
(45) Date of Patent: Sep. 8, 2026

(54) CATHETER ASSEMBLY HOUSING AND RELATED DEVICES AND METHODS

(71) Applicant: Becton, Dickinson and Company, Franklin Lakes, NJ (US)

(72) Inventors: Mukilan Balamurugan, Tamil Nadu (IN); Abinesh Selvam, Tamil Nadu (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 539 days.

(21) Appl. No.: 17/565,192

(22) Filed: Dec. 29, 2021

(65) Prior Publication Data

US 2022/0226616 A1 Jul. 21, 2022

Related U.S. Application Data

(60) Provisional application No. 63/139,668, filed on Jan. 20, 2021.

(51) Int. Cl.
*A61M 25/06* (2006.01)
*A61M 25/00* (2006.01)

(52) U.S. Cl.
CPC .... *A61M 25/0631* (2013.01); *A61M 25/0097* (2013.01); *A61M 25/0606* (2013.01)

(58) Field of Classification Search
CPC .......... A61M 25/0606; A61M 25/0612; A61M 25/0618; A61M 25/0625; A61M 25/0631; A61M 25/0681; A61M 25/0097; A61M 25/0113; A61M 25/01; A61M 2025/018; A61M 2025/0681; A61M 2025/0024; A61M 25/0637
See application file for complete search history.

(56) References Cited

U.S. PATENT DOCUMENTS 4,850,961 A * 7/1989 Wanderer .......... A61M 25/0631 604/110
5,176,650 A * 1/1993 Haining ............ A61M 25/0631 604/164.08
6,090,078 A 7/2000 Erskine
(Continued)

FOREIGN PATENT DOCUMENTS

AU 9027098 A 4/1999
AU 2013315697 A1 4/2015
(Continued)

*Primary Examiner* — Kami A Bosworth
*Assistant Examiner* — Avery Smale
(74) *Attorney, Agent, or Firm* — Kirton McConkie; Whitney Blair; Kevin Stinger

(57) ABSTRACT

A vascular access device may include a housing, a catheter assembly and a needle assembly. The housing includes a proximal end, a distal end, and a slot extending longitudinally therebetween. The catheter assembly includes a catheter hub and a catheter extending distally from the catheter hub, wherein the catheter and the catheter hub are disposed within the housing. The needle assembly includes a needle hub having a translation feature and an introducer needle having a sharp distal tip. The introducer needle extends distally from the needle hub through the catheter. The translation feature is moveable along the slot to translate the needle hub between the proximal end of the housing and the distal end of the housing.

16 Claims, 14 Drawing Sheets

(56) References Cited

U.S. PATENT DOCUMENTS

| | | | | |
|---|---|---|---|---|
| 6,261,264 | B1 | 7/2001 | Tamaro | |
| 10,500,376 | B2 * | 12/2019 | Isaacson | A61M 25/0606 |
| 2002/0107483 | A1 * | 8/2002 | Cook | A61M 25/0618 604/164.01 |
| 2005/0273057 | A1 * | 12/2005 | Popov | A61M 25/0631 604/164.08 |
| 2009/0182259 | A1 * | 7/2009 | Hochberg | A61M 31/00 604/15 |
| 2010/0094310 | A1 * | 4/2010 | Warring | A61M 25/0631 606/108 |
| 2014/0074032 | A1 | 3/2014 | Bornhoft | |
| 2015/0352333 | A1 * | 12/2015 | Arellano Cabrera | A61M 25/0054 604/110 |
| 2015/0359973 | A1 * | 12/2015 | Onken | A61M 5/32 604/164.08 |
| 2016/0067453 | A1 | 3/2016 | Braithwaite et al. | |
| 2017/0028128 | A1 * | 2/2017 | Cole | A61M 25/0606 |
| 2017/0043101 | A1 | 2/2017 | Cole et al. | |
| 2019/0060616 | A1 * | 2/2019 | Solomon | A61M 39/1011 |
| 2020/0330701 | A1 | 10/2020 | Cole et al. | |

FOREIGN PATENT DOCUMENTS

| | | | | |
|---|---|---|---|---|
| BR | 112015005703 | A2 | 7/2017 | |
| CA | 2884740 | A1 | 3/2014 | |
| CA | 2945067 | A1 | 10/2015 | |
| CN | 203539776 | U | 4/2014 | |
| CN | 206518747 | U | 9/2017 | |
| CN | 209187750 | U | 8/2019 | |
| EP | 0397038 | A1 | 11/1990 | |
| EP | 2895230 | A1 | 7/2015 | |
| EP | 3134154 | A1 | 3/2017 | |
| ES | 2690523 | T3 | 11/2018 | |
| JP | 2015531656 | A | 11/2015 | |
| JP | 2017513622 | A | 6/2017 | |
| JP | 6189961 | B2 | 8/2017 | |
| JP | 6618928 | B2 | 12/2019 | |
| JP | 2020022839 | A | 2/2020 | |
| JP | 2021183146 | A | 12/2021 | |
| JP | 7026665 | B2 | 2/2022 | |
| MX | 351919 | B | 11/2017 | |
| WO | 9916488 | | 4/1999 | |
| WO | 2014043125 | A1 | 3/2014 | |
| WO | WO-2014169425 | A1 * | 10/2014 | A61M 25/0631 |
| WO | 2015164653 | | 10/2015 | |

* cited by examiner 36
42
37
39
32
60
58
30
54
62
46
40
45
34

60
58
54
62
36
46
40
37
45
39
32
34

60
54
64
76
46
36
37
48
50
40
45
34

36
42
37
60
32
54
30
46
40
45
34

62

39
44
64
50
48

CATHETER ASSEMBLY HOUSING AND RELATED DEVICES AND METHODS

RELATED APPLICATIONS

This application claims benefit of U.S. Provisional Patent Application No. 63/139,668, filed on Jan. 20, 2021, entitled CATHETER ASSEMBLY HOUSING AND RELATED DEVICES AND METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of a catheter assembly that includes the catheter. After placement of the needle has been confirmed, the clinician may remove the needle, leaving the catheter in place for future blood withdrawal or fluid infusion.

Catheter assembly use tends to generate a significant amount of waste. In addition to packaging needed to ensure sterility of catheter assembly components prior to use, packaging must also enclose safety components intended to be immediately discarded, such as a needle cover. In practice, the needle cover resides over the sharp distal tip of the introducer needle to protect against accidental needle sticks prior to use. The needle cover, however, must be removed and discarded before the needle can be used. Additionally, after the needle is used and removed from the vasculature, both the needle and associated needle hub must also be discarded.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related devices, systems, and methods. In some embodiments, a vascular access device may include a housing having a proximal end, a distal end, and a slot extending longitudinally between the proximal end and the distal end. In some embodiments, the vascular access device may include a catheter assembly including a catheter hub and a catheter extending distally from the catheter hub. In some embodiments, the catheter and the catheter hub may be disposed within the housing.

In one set of example embodiments, the vascular access device may include a needle assembly including a needle hub having a translation feature and an introducer needle having a sharp distal tip. In some embodiments, the introducer needle extends distally from the needle hub through the catheter. In some embodiments, the translation feature is moveable along the slot to translate the needle hub between the proximal end of the housing and the distal end of the housing.

In some embodiments, the catheter hub may extend beyond the distal end of the housing in response to the translation feature moving from a proximal end of the slot to a distal end of the slot. In some embodiments, the needle hub may be maintained within the housing in response to the translation feature moving from the proximal end of the slot to the distal end of the slot.

In some embodiments, an adapter may be coupled to the needle hub. In some embodiments, the adapter may include a distal end, a proximal end, and a compressed tube therebetween. The proximal end of the adapter may be coupled to the needle hub such that the compressed tube expands in response to the needle hub being retracted in a proximal direction within the housing.

In some embodiments, a distal end of the adapter may include a luer connector. In some embodiments, the translation feature may include a tab coupled to the needle hub and extending through the slot. In some embodiments, the housing may include an elongate barrel. In some embodiments, a removable barrier, such as a peel foil, may be coupled to the distal end of the housing.

In some embodiments, the translation may be configured to move along the slot in a distal direction to advance the introducer needle and may be configured to move along the slot in a proximal direction to retract the introducer needle. In some embodiments, the housing may include a lock mechanism to selectively secure the adapter in position relative to the housing. In some embodiments, at least a portion of the lock mechanism may be disposed at the distal end of the housing.

In some embodiments, the vascular access device may include a vent plug disposed within the needle hub and configured to allow air to exit the needle hub. In some embodiments, the adapter may include a catheter hub lock to secure a position of the catheter hub relative to the adapter.

In a second set of example embodiments, a method for advancing and shielding a needle may include advancing a translation feature distally along a vascular access device to advance a catheter into a vasculature of a patient. In some embodiments, the vascular access device may include a housing, a catheter assembly, and a needle assembly. In some embodiments, the housing may include a proximal end, a distal end, and a slot extending longitudinally between the proximal end and the distal end. In some embodiments, the catheter assembly may include a catheter hub and a catheter extending distally therefrom. In some embodiments, at least a portion of the catheter assembly may be disposed within the housing.

In some embodiments, the needle assembly may include a needle hub, an introducer needle extending distally from the needle hub through the catheter, and a translation feature coupled to the needle hub and configured to move longitudinally along the slot to translate the needle hub within the housing. In some embodiments, the introducer needle and the catheter may be configured to advance beyond the distal end of the housing in response to the translation feature moving distally along the slot.

In some embodiments, the vascular access device may further include an adapter coupled to the needle hub. In some embodiments, the adapter may include a distal end, a proximal end, and a compressed tube therebetween. In some embodiments, the method may include securing a position of a distal end of the adapter relative to the distal end of the housing in response to the translation feature being disposed proximate to the distal end of the slot. In some embodiments, the translation feature may be retracted in a proximal direction along to retract the needle hub within the housing. In some embodiments, a length of the compressed tube within the housing may be expanded in response to retracting the translation feature. In some embodiments, the method may include shielding the introducer needle within the compressed tube in response to retracting the translation feature along the slot.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
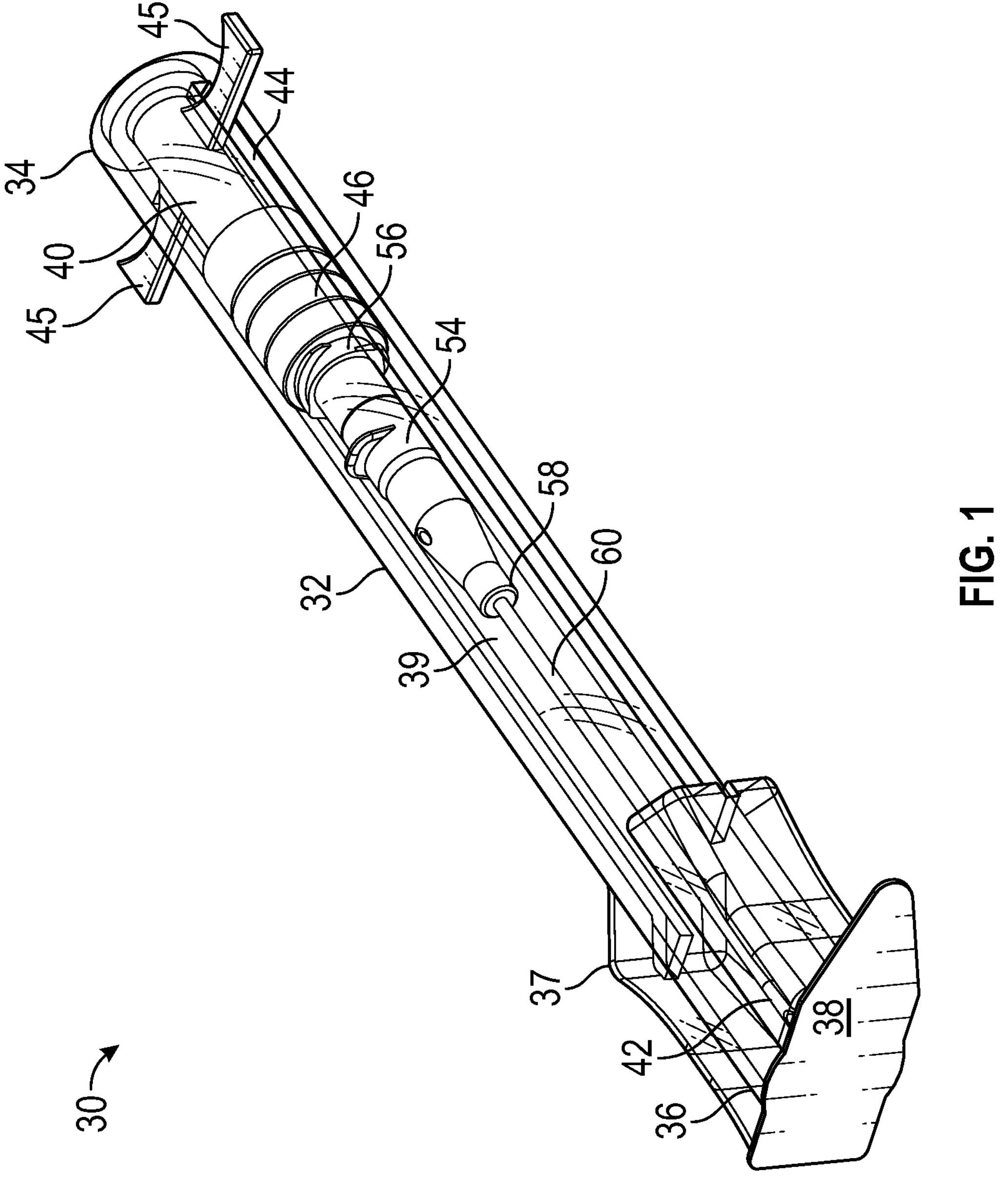
FIG. 1 is an upper perspective view of an example vascular access device, according to some embodiments.
Figure 2:
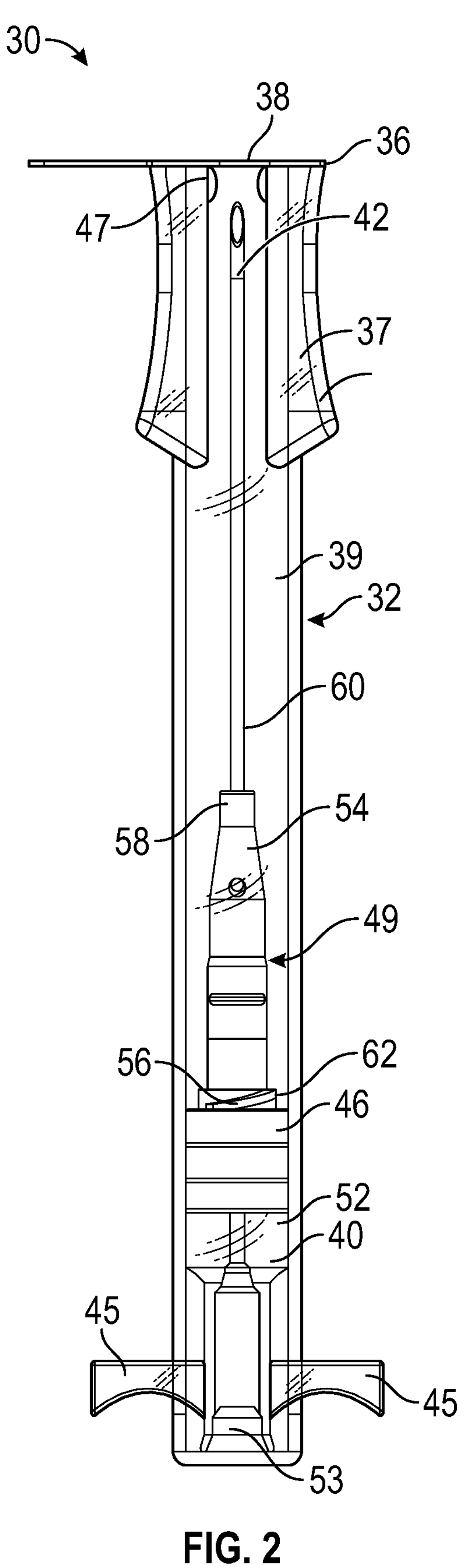
FIG. 2 is a top view of the vascular access device of FIG. 1, according to some embodiments.
Figure 3:
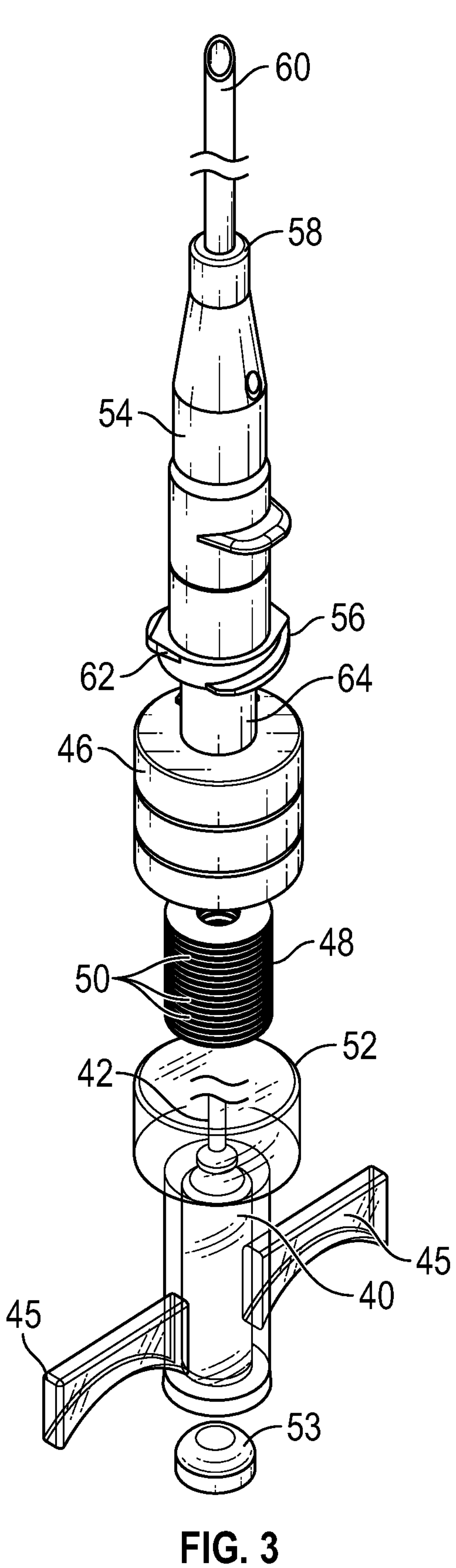
FIG. 3 is an exploded view of an example needle assembly, an example catheter assembly, and an example adapter of the vascular access device of FIG. 1, according to some embodiments.
Figure 4:
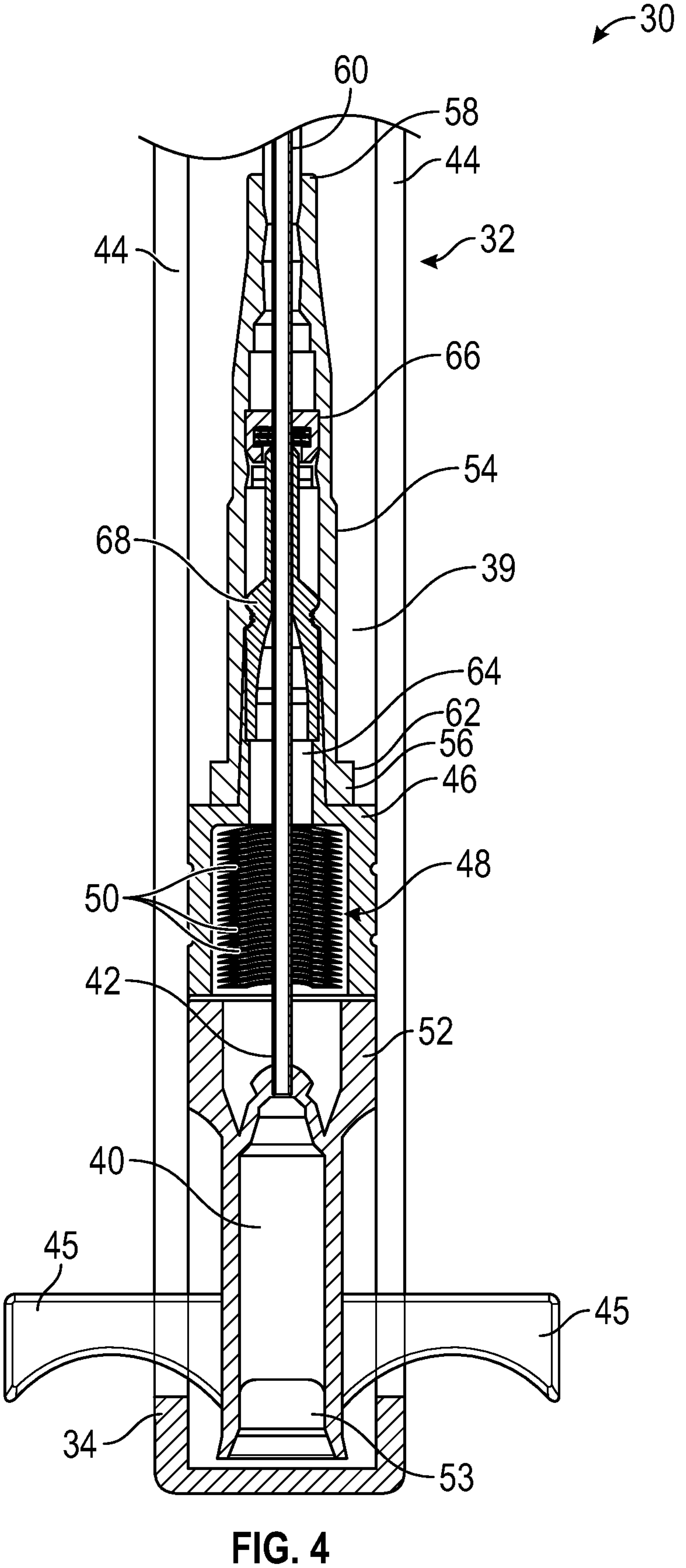
FIG. 4 is a cross-sectional view of the vascular access device of FIG. 1, according to some embodiments.

Referring now to FIGS. 1-4, in some embodiments, a vascular access device 30 may include a housing 32 extending along a longitudinal axis and having a proximal end 34 and a distal end 36. In some embodiments, the housing 32 may monolithically formed as a single unit and/or may include a rigid material such as a biocompatible polymer or another suitable material. In some embodiments, the housing 32 may include an elongate barrel shape or another suitable shape.

In some embodiments, the grip element 37 may be disposed towards the distal end 36 of the housing 32 to accommodate a user's grasp. In some embodiments, the grip element 37 may extend laterally from opposing sides of the housing 32. In these and other embodiments, the grip element 37 may include one or more textured surfaces to facilitate the user's grip.

In some embodiments, a removable barrier 38 may be coupled to the distal end 36 of the housing 32 to maintain sterility of internal components. In some embodiments, the removable barrier 38 may be disposable and may be coupled to the housing 32 via an adhesive, press fit, or other suitable mechanism. In some embodiments, for example, the removable barrier 38 may include foil or another material configured to be peeled back or otherwise easily removed by the user. For example, in some embodiments, the removable barrier 38 may include foil, plastic, paper, composite, or any other suitable disposable material. Some embodiments of the removable barrier 38 may be coupled to the housing 32 via a press fit or another suitable mechanism to protect the sterility of internal components. In some embodiments, the removable barrier 38 may include a pull tab or other feature or device coupled to or integrated with the removable barrier 38 to facilitate quick and easy removal.

In some embodiments, the housing 32 may include a lumen 39 extending along the longitudinal axis between the proximal end 34 and the distal end 36. In some embodiments, the lumen 39 may include a shape and dimensions to accommodate various internal components. In some embodiments, for example, the vascular access device 30 may include a needle assembly having a needle hub 40 and a needle 42 extending distally therefrom. In some embodiments, the needle hub 40 may be slidably disposed within the lumen 39. In some embodiments, the needle hub 40 may be coupled to a proximal end of the needle 42 such that a sharp distal tip of the needle 42 may extend from the distal end of the housing 32 to selectively access a patient's vasculature.

In some embodiments, one or more slots 44 may extend from an interior surface to an exterior surface of the housing 32. In some embodiments, the slots 44 may extend longitudinally along the housing 32 between the distal end 36 and the proximal end 34.

In some embodiments, the needle assembly may include a translation feature such as one or more tabs 45 extending outwardly from the needle hub 40. In some embodiments, the one or more tabs 45 may extend through the slots 44 to enable a user to access the tabs 45 to translate the needle hub 40 along the longitudinal axis within the housing 32. As illustrated, in some embodiments, the tabs 45 may extend laterally from opposing sides of the needle hub. Some embodiments of the tabs 45 may be generally planar or wing-like to facilitate manual manipulation of the tabs 45 and associated translation of the needle hub 40.

In some embodiments, the distal end 36 of the housing 32 may include a lock mechanism to secure a position of an adapter 46 relative to the housing 32. In some embodiments, the lock mechanism may include a mechanical locking device or other feature coupled to or integrated with the distal end 36 of the housing 32. For example, in some embodiments, a distal end of the lumen 39 may include one or more protrusions 47, notches, grooves, or other suitable features to engage a corresponding feature of the adapter 46. In some embodiments, the lock mechanism may be actuated by adjusting or manipulating a proximal end of the needle hub 40 by, for example, retracting the needle hub 40 in a proximal direction and/or laterally rotating the needle hub 40 within the lumen 39.

In some embodiments, the internal components of the housing 32 may include one or more of the following: the needle assembly, the adapter 46 including a compressed tube 48, and a catheter assembly 49. In some embodiments, the compressed tube 48 may include multiple extendable folds 50. In some embodiments, the needle hub 40 may include a collar 52 at a distal end of the needle hub 40 and configured to couple to a proximal end of the adapter 46. In some embodiments, the needle 42 may extend through the collar 52. In some embodiments, a vent plug 53 may be coupled to a proximal end of the needle hub 40, as discussed in more detail below.

In some embodiments, the catheter assembly 49 may include a catheter hub 54, which may include a proximal end 56, a distal end 58, and a lumen extending therethrough. In some embodiments, the catheter assembly 49 may include a catheter 60, which may extend distally from the distal end 58 of the catheter hub 54. In some embodiments, the catheter 60 may include a peripheral intravenous catheter, a peripherally-inserted central catheter, or a midline catheter. In some embodiments, the proximal end 56 of the catheter hub 54 may include a luer connector, such as the female luer connector 62 illustrated.

In some embodiments, the distal end of the adapter 46 may include a luer connector 64 configured to engage a corresponding luer connector 62 of the catheter hub 54. In some embodiments, the distal end of the adapter 46 may include a male luer connector 64 configured to engage a corresponding female luer connector 62 of the catheter hub 54. In some embodiments, a septum 66 and/or a septum actuator 68 may be disposed within the catheter hub 54.

In some embodiments, the needle 42 may extend from a distal end of the needle hub 40. In some embodiments, the needle 42 may extend through the internal components when the needle hub 40 is in a ready position. In some embodiments, translating the needle hub 40 in a distal direction within the housing 32 may push the internal components distally such that at least a portion of the catheter hub 54, the catheter 60, and/or the needle 42 may extend distal to the distal end 36 of the housing 32. In this position, the catheter 60 may be ready for insertion into the vasculature of a patient.

In some embodiments, a distal end of the compressed tube 48 may be secured within a distal end of the adapter 46. In some embodiments, a proximal end of the compressed tube 48 may be secured to the collar 52 and/or distal end of the needle hub 40. In some embodiments, the compressed tube 48 may include silicone, food grade silicone or another suitable material. In some embodiments, the extendable folds 50 may be corrugated, similar to an expandable straw. In some embodiments, the extendable folds 50 may be configured such that the extendable folds 50 contact or are disposed in close proximity to each other when the needle hub 40 is in the ready position such that the needle hub 40 contacts the adapter 46.

In some embodiments, the extendable folds 50 may be configured to flatten and separate in response to the needle hub 40 being retracted within the housing 32. In some embodiments, the needle hub 40 may be longitudinally distanced from the adapter 46 in the retracted position.

In some embodiments, the compressed tube 48 may increase in length in response to the needle hub 40 being retracted within the housing 32. In some embodiments, the length of the compressed tube 48 may increase such that the compressed tube 48 may shield a length of the needle 42 within the lumen 39. In some embodiments, the extendable folds 50 may result in the compressed tube 48 having a greater cross-sectional diameter in the ready position than in the retracted position.

Figure 5A:
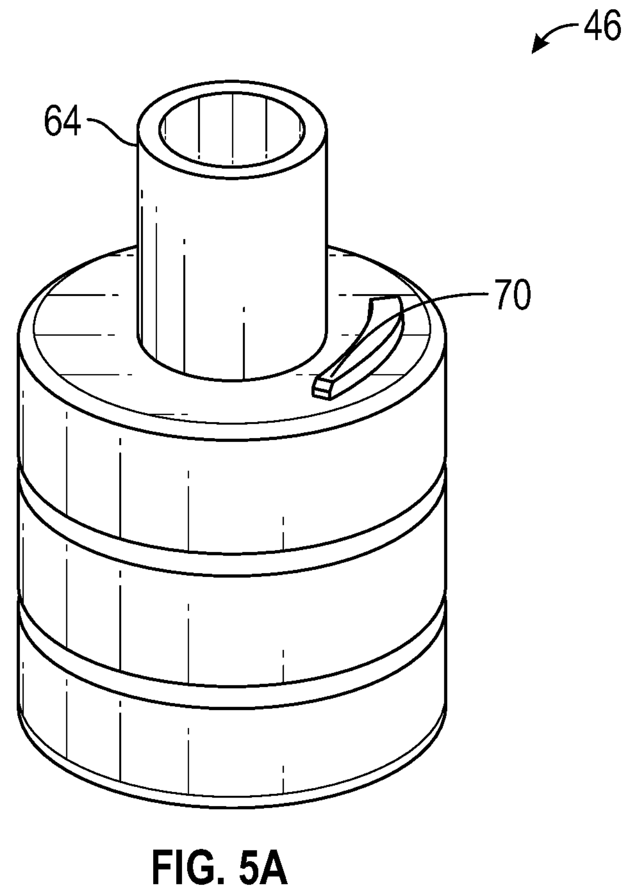
FIG. 5A is an upper perspective view of the adapter of FIG. 3, according to some embodiments.
Figure 5B:
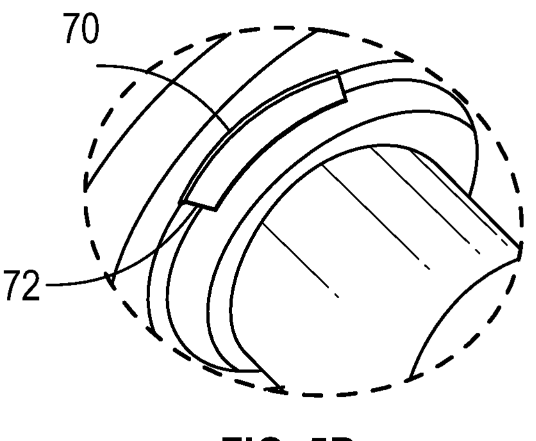
FIG. 5B is a distal end view of a portion of the adapter of FIG. 3, according to some embodiments.

Referring now to FIGS. 5A-5B, in some embodiments, the adapter 46 may include a catheter hub lock 70 to prevent or limit rotational movement between the adapter 46 and the catheter hub 54. In some embodiments, the catheter hub lock 70 may be coupled to or integrated with a distal end of the luer connector 64. In some embodiments, the catheter hub lock 70 may include a protrusion or other feature configured to mechanically engage a corresponding feature such as an aperture 72 disposed on a proximal end of the catheter hub 54. In some embodiments, the protrusion may engage the aperture 72 in response to rotation of the adapter 46 relative to the catheter hub 54. In some embodiments, the catheter hub lock 70 may thereby secure a position of the adapter 46 with respect to the catheter hub 54.

Figure 6:
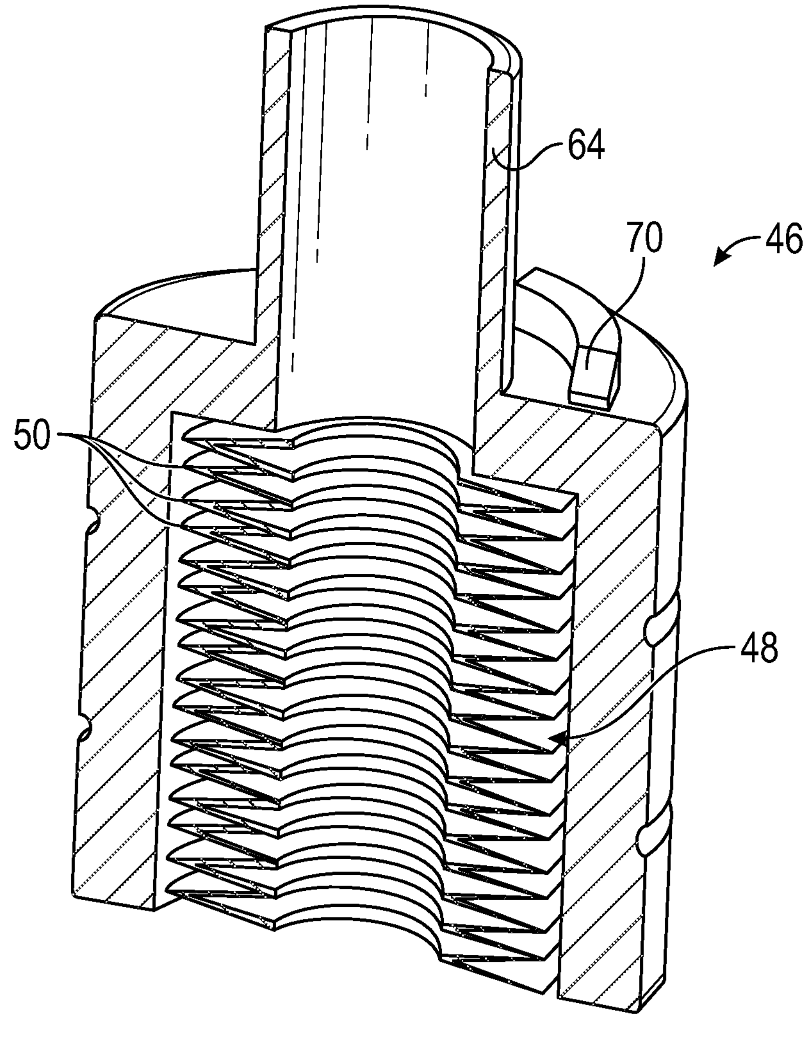
FIG. 6 is a cross-sectional view of the adapter of FIG. 3, according to some embodiments.

Referring now to FIG. 6, in some embodiments, the compressed tube 48 may be retained within the adapter 46 such that a distal end of the compressed tube 48 may be disposed proximal to the luer connector 64. In some embodiments, the distal end of the compressed tube 48 may be coupled to an interior surface of the adapter 46 via an adhesive, a press fit, or by any other suitable mechanism or device.

Figure 7A:
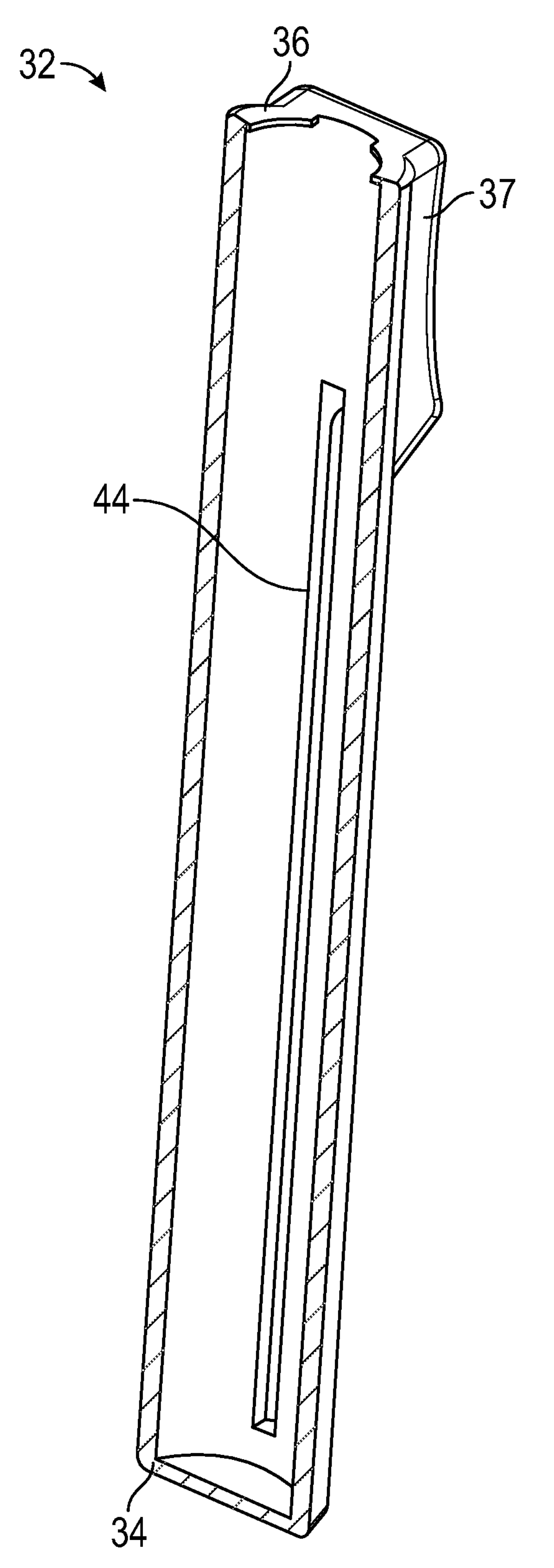
FIG. 7A is a cross-sectional view of an example housing, according to some embodiments.
Figure 7B:
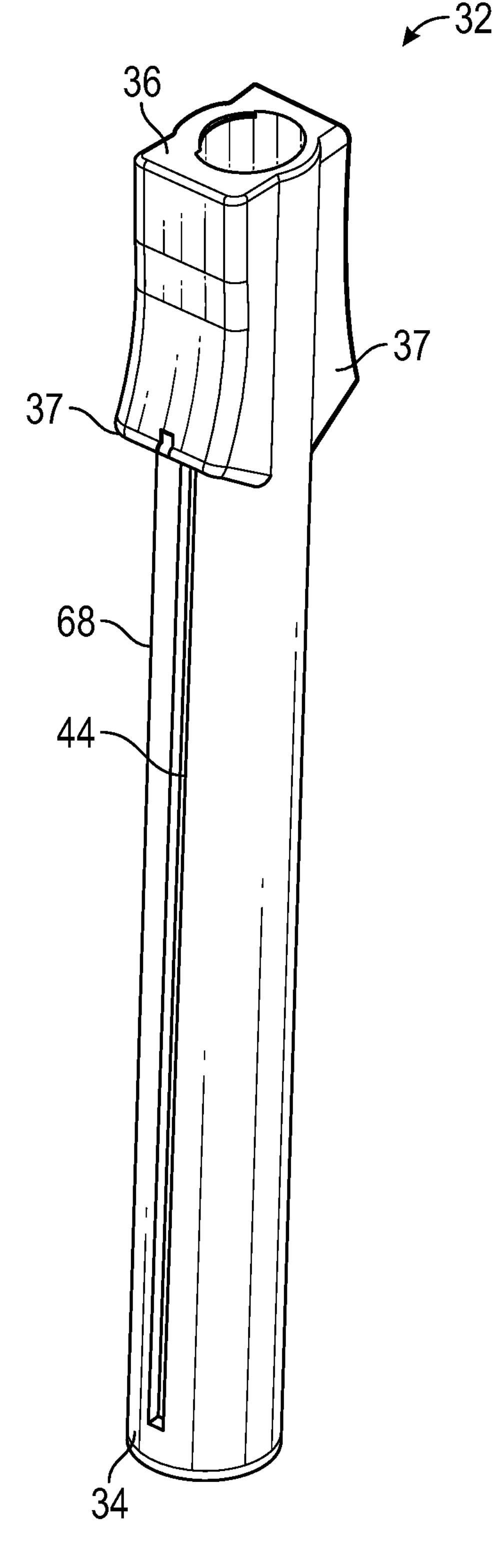
FIG. 7B is a perspective view of the housing of FIG. 7A, according to some embodiments.

Referring now to FIGS. 7A-7B, in some embodiments, one or more slots 44 may be disposed between the proximal end 34 and the distal end 36 of the housing 32. In some embodiments, as illustrated herein, the housing 32 may include an elongate barrel-shaped body. In some embodiments, a grip element 37 may be coupled to or integrated with the distal end 36 of the body of the housing 32. In some embodiments, a distal end of the slot 44 may be disposed within or proximate to a proximal end of the grip element 37. In some embodiments, the grip element 37 may thereby provide a distal stop for the translation feature or tab 45, for example. In some embodiments, engagement of the translation feature or tab 45 with the grip element 37 may provide a snap lock to secure a position of the needle hub 40 relative to the housing 32.

Similarly, in some embodiments, a proximal end of one or more of the slots 44 may include a snap lock or other mechanism to engage the needle hub 40 and/or the translation feature or tab 45 when the needle hub 40 is in the retracted position. In some embodiments, the snap lock may selectively engage and secure the needle hub 40 and/or the translation feature or tabs 45 relative to the housing 32. In some embodiments, the slot 44 may narrow such that the tab 45 may snap past the narrowing to lock into place relative to the housing 32.

In some embodiments, the translation feature or tabs 45 may be translated in a distal direction to advance the catheter assembly 49, the adapter 46, and the needle assembly through the housing 32. In some embodiments, the tabs 45 may be translated in a proximal direction along the housing 32 to retract the needle 42 through the catheter assembly 49 and separate the needle hub 40 from the adapter 46.

Figure 8A:
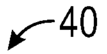
FIG. 8A is a top view of an example needle hub, according to some embodiments.
Figure 8A:
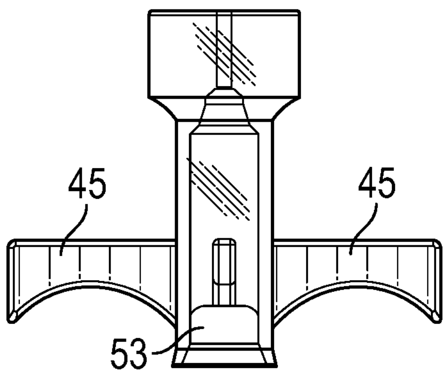
Figure 8B:
FIG. 8B is a cross-sectional view of the needle hub of FIG. 8A, according to some embodiments.
Figure 8B:
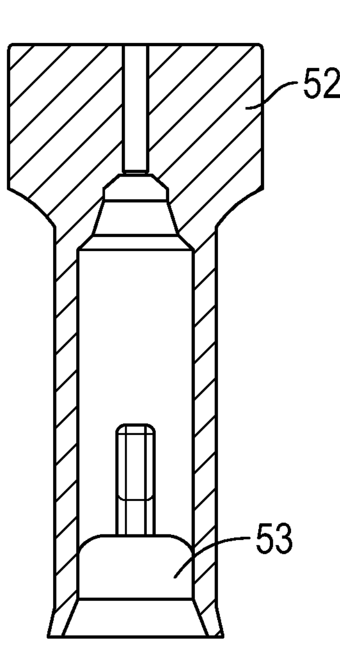

Referring now to FIGS. 8A-8B, in some embodiments, the needle hub 40 may include a vent plug 53 disposed at or near its proximal end. In some embodiments, the vent plug 53 may be configured to allow air but not fluid to exit the needle hub 40. In some embodiments, the vent plug 53 may include a porous material or membrane.

Referring now to FIGS. 9-18, example embodiments of a method for using a vascular access device 30 to advance a catheter and shield an introducer needle after use are illustrated. FIGS. 9-13 illustrate embodiments of the vascular access device 30 that include multiple translation features or tabs 45. FIGS. 14-18, on the other hand, illustrate embodiments of the vascular access device 30 that include a single translation feature or tab 45.

Figure 9:
FIG. 9 is an upper perspective view of the vascular access system of FIG. 1, illustrating a user peeling away an example removable barrier, according to some embodiments.
Figure 9:
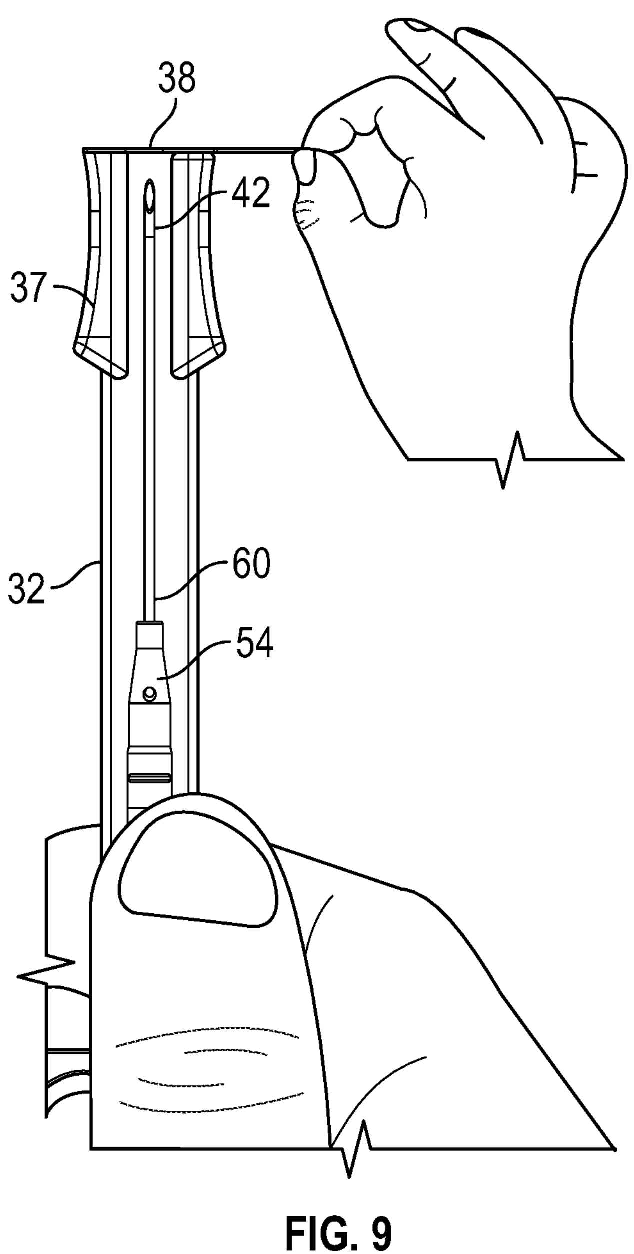
Figures 10, 11, 12:
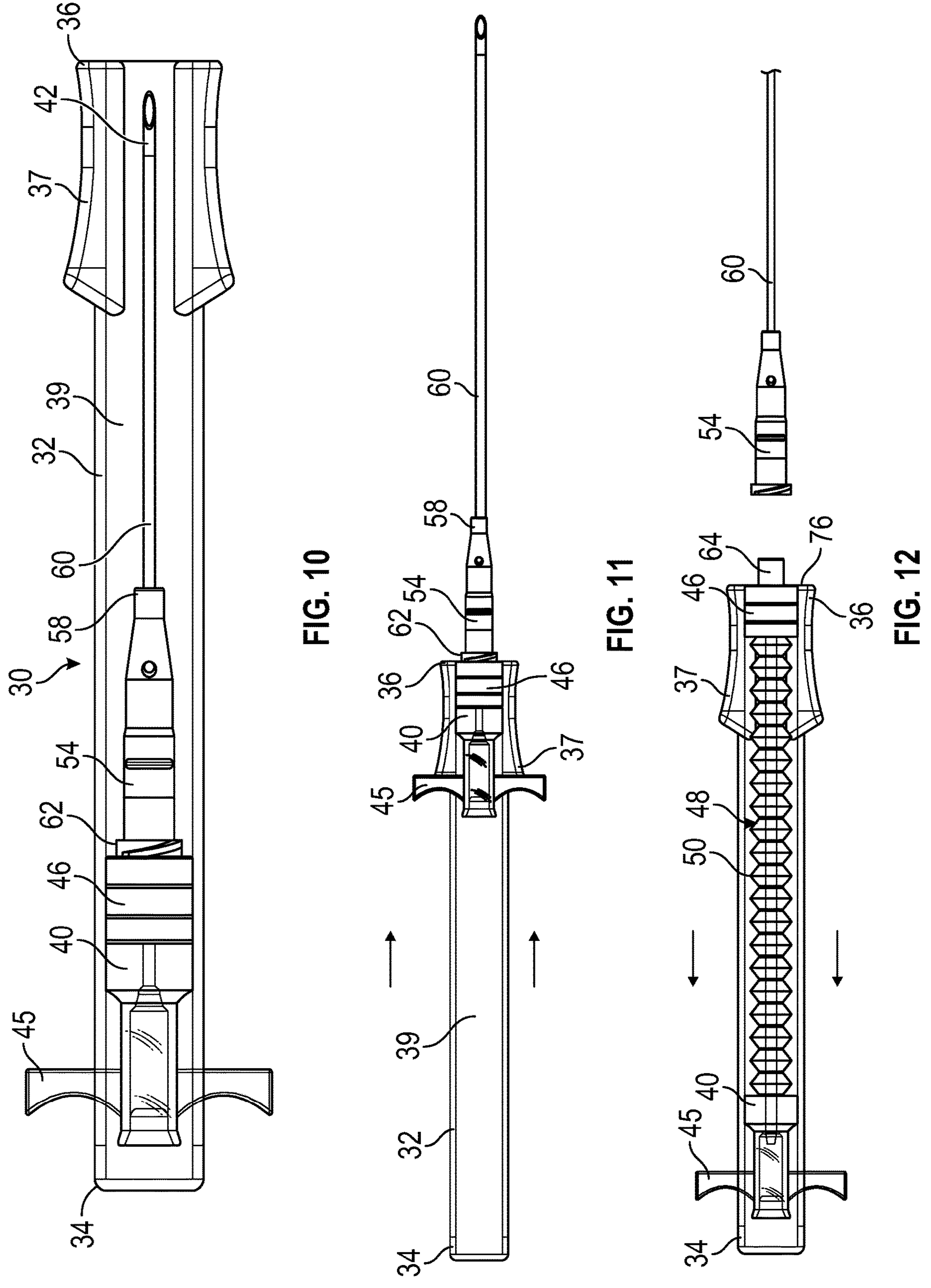
FIG. 10 is a top view of the vascular access device of FIG. 1, illustrating the needle hub in an example ready position, according to some embodiments.
FIG. 11 is an upper perspective view of the vascular access device of FIG. 1, illustrating the needle hub in an example use position, according to some embodiments.
FIG. 12 is an upper perspective view of the vascular access device of FIG. 1, illustrating the needle hub in an example retracted position, according to some embodiments.
Figure 14:
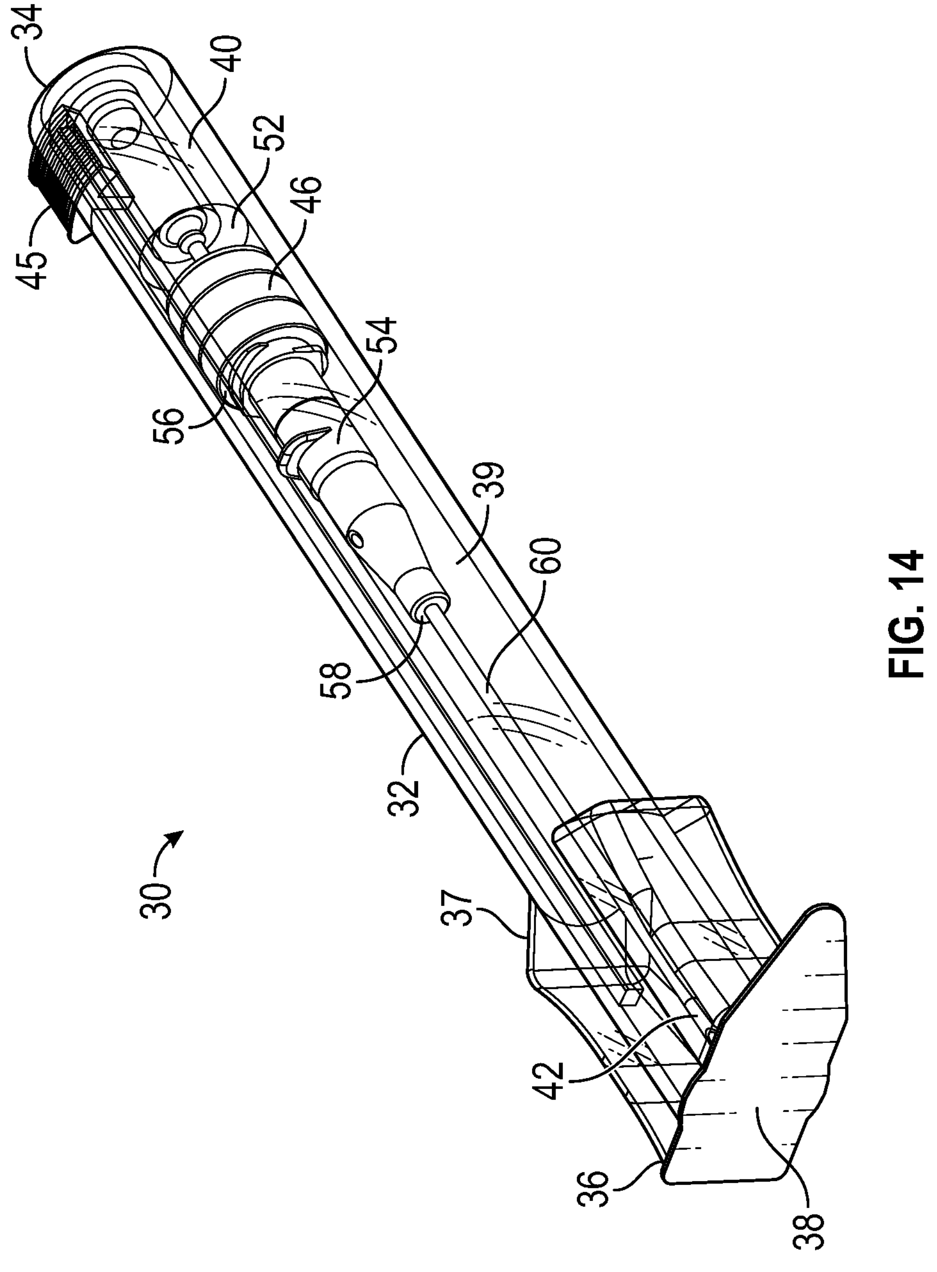
FIG. 14 is an upper perspective view of another example vascular access device, according to some embodiments.
Figures 15, 16, 17:
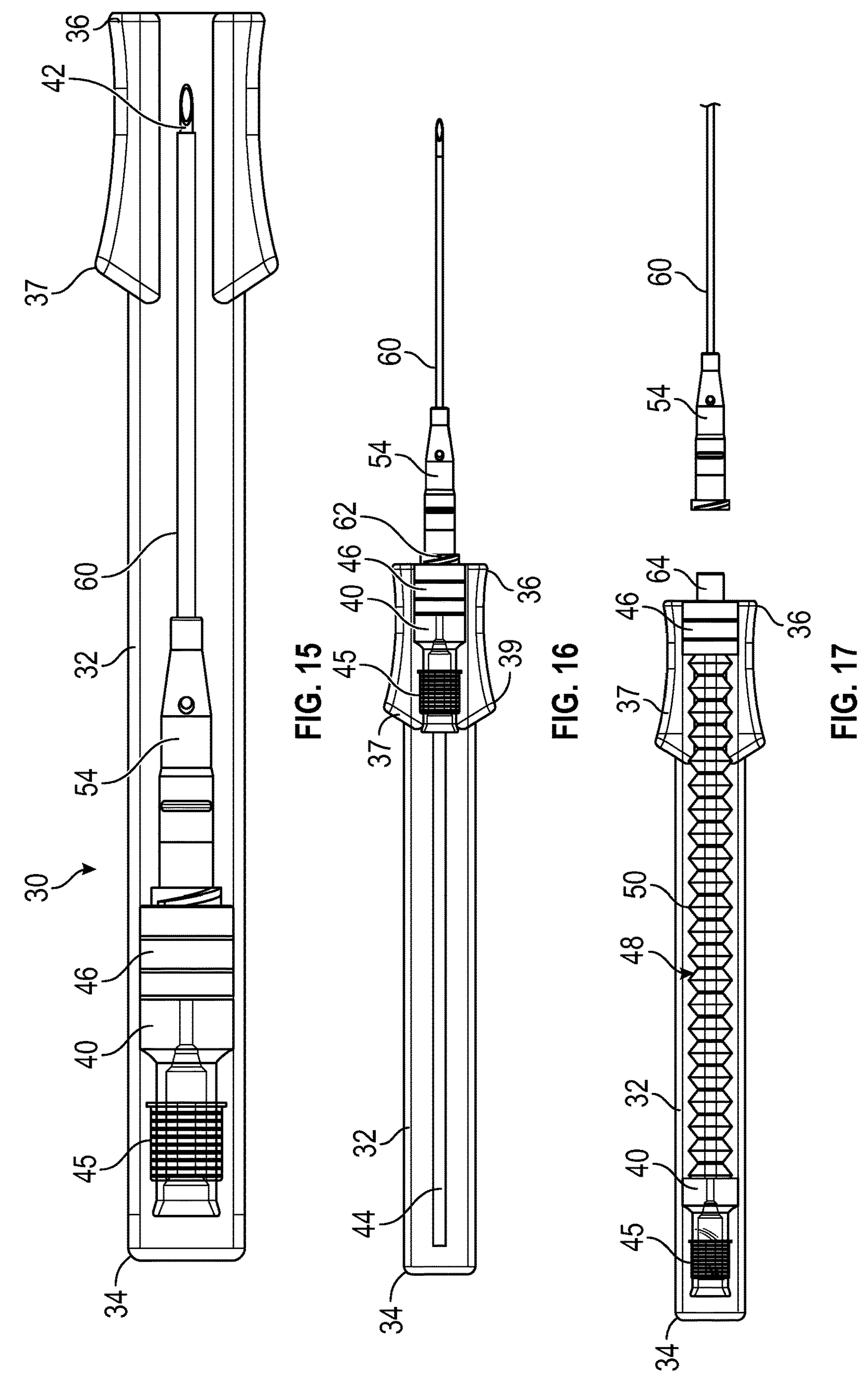
FIG. 15 is a top view of the vascular access device of FIG. 14, illustrating the needle hub in the ready position, according to some embodiments.
FIG. 16 is an upper perspective view of the vascular access device of FIG. 14, illustrating the needle hub in the use position, according to some embodiments.
FIG. 17 is an upper perspective view of the vascular access device of FIG. 14, illustrating the needle hub in the retracted position, according to some embodiments.

As shown in FIGS. 9 and 14, some embodiments may include removing and/or discarding a removable barrier 38 from the distal end 36 of the housing 32. In some embodiments, the vascular access device 30 may include a needle having a sharp distal tip disposed within the housing 32 prior to use for safety. As shown in FIGS. 11 and 16, a user may grip the translation feature or tabs 45 to translate the needle hub 40 in a distal direction within the housing 32. In some embodiments, this may also move the needle, the catheter assembly 49, and the adapter 46 distally within the housing 32.

In this manner, in some embodiments, the needle hub 40 may be distally translated to a ready position such that the sharp distal tip 24 of the needle 42 may extend beyond the distal end 36 of the housing 32. In some embodiments, the sharp distal tip 24 of the needle 42 may then be manipulated to break tip adhesion such that the sharp distal tip 24 may penetrate the vasculature. In these and other embodiments, the catheter 60 may be advanced into the vasculature in response to entry of the needle 42 into the vasculature. In some embodiments, entry of the catheter 60 into the vasculature may be confirmed by verifying blood flashback. For example, in some embodiments, blood flashback may flow distally through the needle 42 and out of a notch in the needle 42 into a space between the needle 42 and the catheter 60. In some embodiments, blood flashback may flow into a flashback chamber.

Referring now to FIGS. 12 and 17, in some embodiments, the needle 42 may be removed from the vasculature after blood flashback has been confirmed. In some embodiments, the needle 42 may be removed by retracting the needle hub 40 in a proximal direction. In some embodiments, the translation feature or one or more tabs 45 may be gripped by the user and moved in the proximal direction along the slots 44 to retract the needle hub 40 and associated needle 42.

In some embodiments, the lock mechanism may be actuated to secure the adapter 46 at the distal end 36 of the housing 32. In some embodiments, the lock mechanism may be actuated by any mechanical, electrical, magnetic, or other suitable mechanism or device. In some embodiments, the lock mechanism may include a groove, indentation, protrusion, or other device or feature configured to engage or interact with the adapter 46 to retain the adapter 46. In some embodiments, the lock mechanism may include a groove, indentation, protrusion or other device or feature configured to engage or interact with the needle hub 40 upon retraction of the needle 42 to retain the needle hub 40 in the retracted position proximate to the proximal end 34 of the housing 32.

In some embodiments, as discussed previously, the distal end of the adapter 46 may be secured at the distal end 36 of the housing 32 upon insertion of the needle 42 into a patient's vasculature. In some embodiments, the needle hub 40 may then be retracted in a proximal direction to retract the needle 42 from the vasculature. In some embodiments, the proximal end of the adapter 46 may be coupled to the needle hub 40 such that retracting the needle hub 40 causes the extendable folds 50 of the tube 48 to expand. In this manner, in some embodiments, the length of the tube 48 may be extended such that at least a portion of the needle 42 may be shielded within tube 48. In some embodiments, the sharp distal tip of the needle 42 may also be shielded within the tube 48 and housing 32 to protect the user from an accidental needle stick.

In some embodiments, securing the adapter 46 to the distal end 36 of the housing 32 may enable the catheter hub 54 to be uncoupled from the adapter 46. In some embodiments, the catheter 60 may remain within the vasculature of the patient for blood draw or infusion thereafter. In some embodiments, the adapter 46 may be secured proximate to the distal end 36 of the housing 32 such that the adapter 46 at least partially covers the distal end 36.

Figure 13:
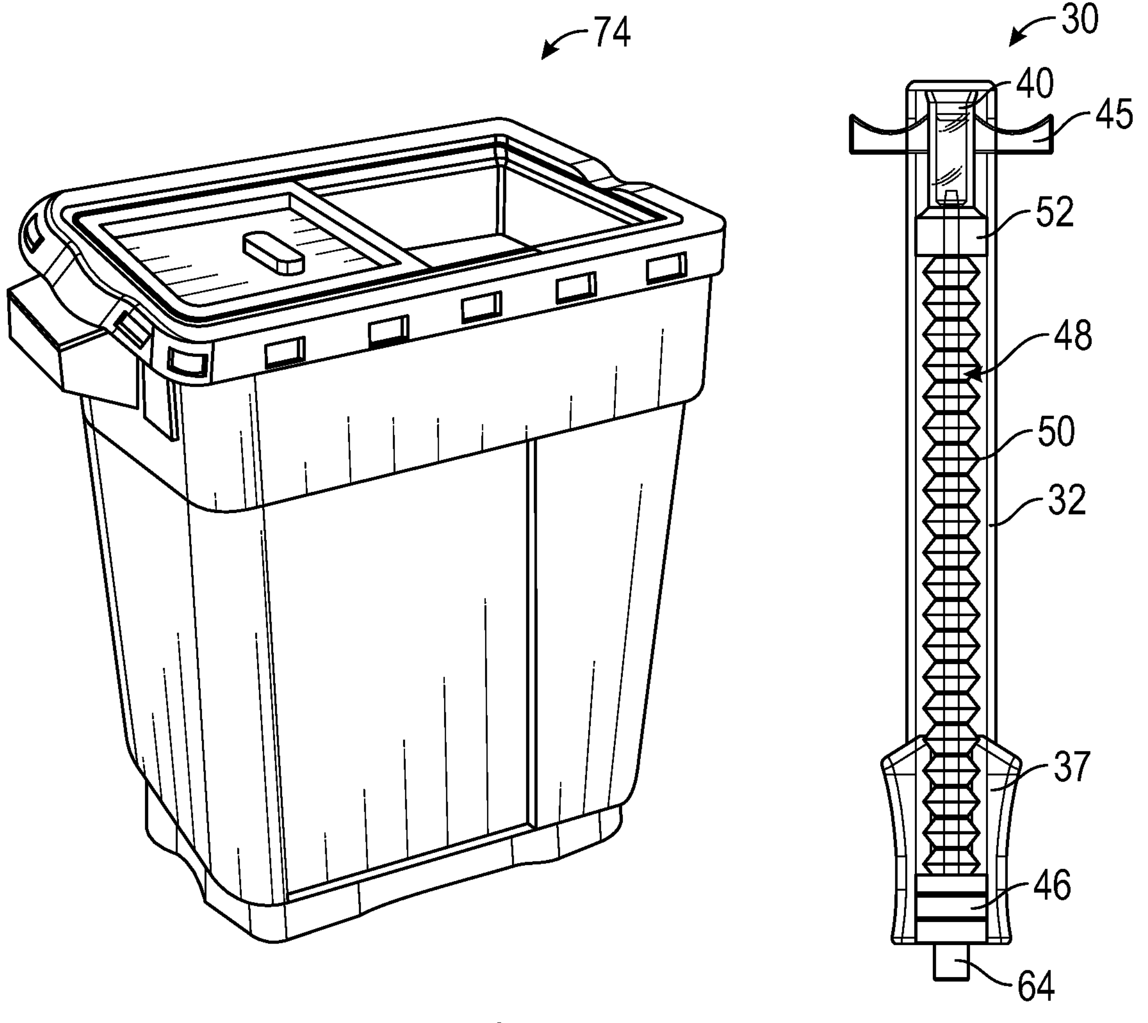
FIG. 13 is a top view of the vascular access device of FIG. 1 after use, illustrating disposal of a portion of the vascular access device, according to some embodiments.
Figure 18:
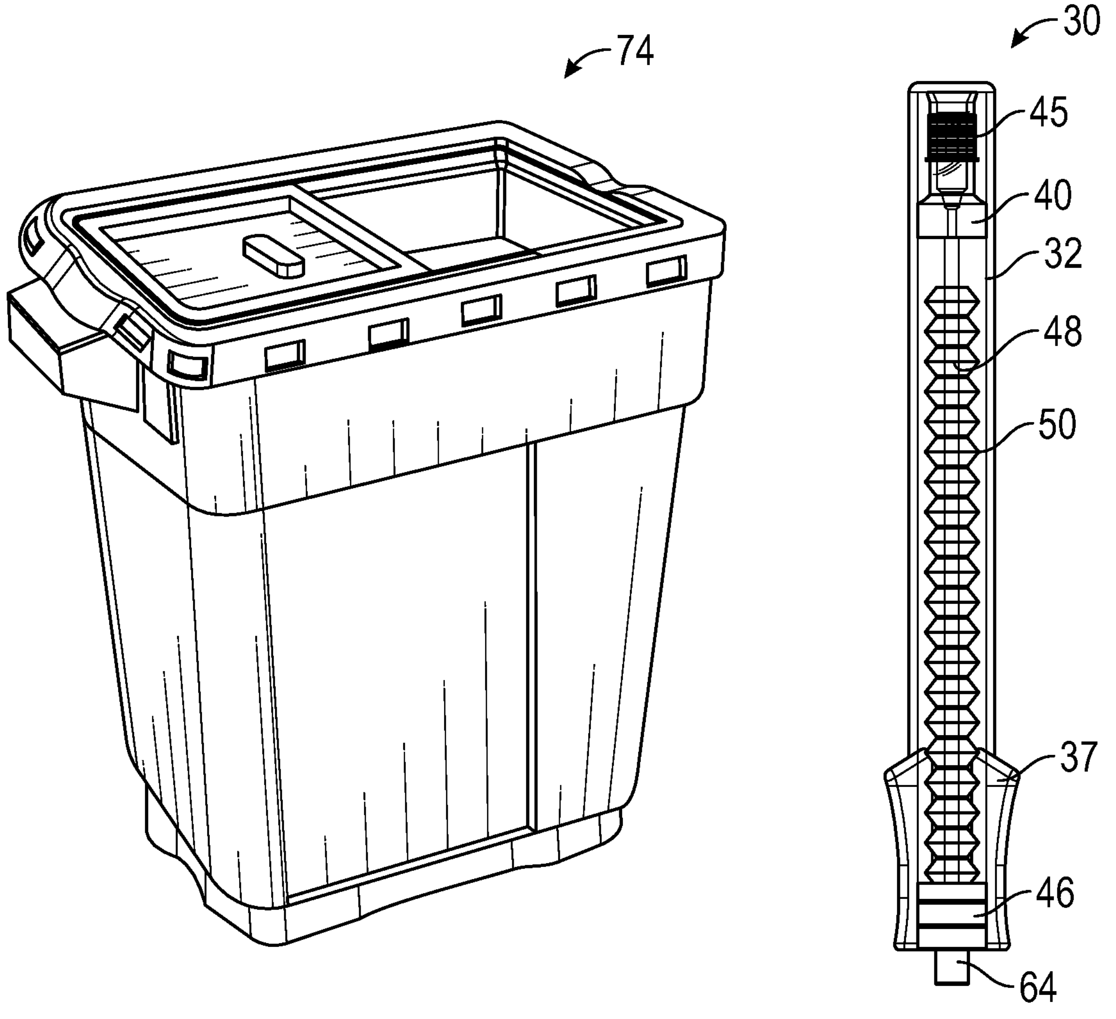
FIG. 18 is a top view of the vascular access device of FIG. 14 after use, illustrating disposal of a portion of the vascular access device, according to some embodiments.

Referring now to FIGS. 13 and 18, in some embodiments, the vascular access device 30 and internal components may be discarded into a trash receptacle 74 after use. In some embodiments, the needle hub 40 may be secured at the proximal end 34 of the housing 32 after retracting the needle 42 from the vasculature. As a result, in some embodiments, the housing 32 may contain the needle hub 40, needle 42, and adapter 46 after use. In some embodiments, the catheter hub 54 may be disengaged from the adapter 46 at the distal end of the housing 32 and the housing 32 and internal components may be discarded as a single unit to safely and effectively prevent exposure to blood and pathogens.

Figure 19:
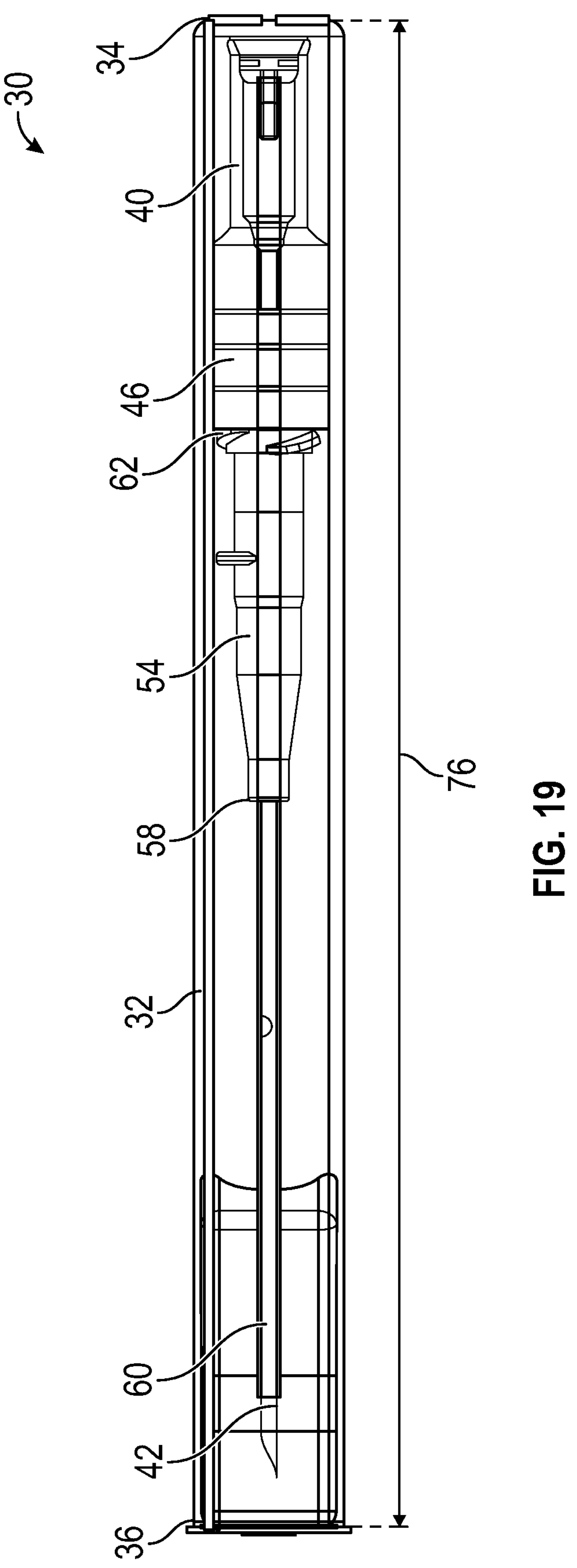
FIG. 19 is a top view of another example vascular access device, according to some embodiments.

Referring now to FIG. 19, some embodiments of the vascular access device 30 may significantly reduce packaging and product materials associated with prior art devices. For example, in some embodiments, total product length 76 of embodiments of the vascular access device 30 may be reduced by about 3.15 inches relative to prior art assemblies. Similarly, in some embodiments, mass measurements of components of the vascular access device 30 may be likewise reduced. Gross weight of some embodiments of the vascular access device 30 may be reduced by about 2.62 grams. These reductions in size, mass, and weight may be due at least in part to elimination of various prior art components, such as the prior art needle cover, for example. In some embodiments, packaging size and material usage may also be reduced relative to prior art devices.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A vascular access device, comprising:

a housing comprising a proximal end, a distal end, and a slot extending longitudinally between the proximal end and the distal end;

a catheter assembly, comprising:

a catheter hub; and a catheter extending distally from the catheter hub, wherein the catheter and the catheter hub are disposed within the housing;

a needle assembly comprising a needle hub having a translation feature and an introducer needle having a sharp distal tip, wherein the introducer needle extends distally from the needle hub through the catheter, wherein the translation feature is moveable along the slot to translate the needle hub between the proximal end of the housing and the distal end of the housing;

an adapter disposed in between the catheter hub and the needle hub, wherein the adapter comprises a distal end and a proximal end, and one or more locking features extending distally from a surface of the adapter and configured to engage one or more corresponding features defined in a surface of the catheter hub to limit rotational movement between the adapter and the catheter hub, wherein the proximal end of the adapter is fixed with respect to the distal end of the adapter; and a corrugated tube compressed within the adapter and comprising a distal end secured to the adapter and disposed within the adapter, wherein in response to movement of the translation feature in a distal direction along the slot, the adapter is configured to slide distally within the housing and to lock to the distal end of the housing, wherein in response to movement of the translation feature in a proximal direction along the slot with the adapter locked to the distal end of the housing, the corrugated tube is configured to expand to shield the introducer needle within the corrugated tube and extends between the needle hub and the adapter.

2. The vascular access device of claim 1, wherein in response to moving the translation feature from a proximal end of the slot to a distal end of the slot, the catheter hub extends beyond the distal end of the housing.

3. The vascular access device of claim 1, wherein in response to moving the translation feature from a proximal end of the slot to a distal end of the slot, the needle hub is maintained within the housing.

4. The vascular access device of claim 1, wherein the distal end of the adapter comprises a luer connector coupled to the catheter hub.

5. The vascular access device of claim 1, wherein the slot is a first slot, wherein housing comprises a second slot extending longitudinally between the proximal end of the housing and the distal end of the housing, wherein the translation feature comprises a first tab coupled to the needle hub and extending through the first slot, wherein translation feature further comprises a second tab coupled to the needle hub and extending through the second slot.

6. The vascular access device of claim 1, wherein the housing comprises an elongate barrel.

7. The vascular access device of claim 1, further comprising a removable barrier coupled to the distal end of the housing.

8. The vascular access device of claim 7, wherein the removable barrier comprises a peel foil.

9. The vascular access device of claim 1, wherein the translation feature is configured to move along the slot in the distal direction to advance the introducer needle and is configured to move along the slot in the proximal direction to retract the introducer needle.

10. The vascular access device of claim 1, wherein the housing further comprises a lock mechanism configured to selectively secure the adapter in position relative to the housing.

11. The vascular access device of claim 10, wherein at least a portion of the lock mechanism is disposed at the distal end of the housing.

12. The vascular access device of claim 1, further comprising a vent plug disposed within the needle hub, wherein the vent plug is configured to allow air to exit the needle hub.

13. A method for advancing and shielding an introducer needle, comprising:

advancing a translation feature in a distal direction along a slot of a housing of a vascular access device, the vascular access device comprising:

the housing comprising a proximal end, a distal end, and the slot extending longitudinally between the proximal end and the distal end;

a catheter assembly comprising a catheter hub and a catheter extending distally from the catheter hub, wherein at least a portion of the catheter assembly is disposed within the housing; and a needle assembly comprising a needle hub, the introducer needle extending distally from the needle hub through the catheter, and the translation feature coupled to the needle hub and configured to move longitudinally along the slot to translate the needle hub within the housing, wherein in response to advancing the translation feature in the distal direction along the slot, the introducer needle and the catheter are configured to advance beyond the distal end of the housing;

an adapter disposed in between the catheter hub and the needle hub, wherein the adapter comprises a distal end and a proximal end, and one or more locking features extending distally from a surface of the adapter and configured to engage one or more corresponding features defined in a surface of the catheter hub to limit rotational movement between the adapter and the catheter hub, wherein the proximal end of the adapter is fixed with respect to the distal end of the adapter; and a corrugated tube compressed within the adapter and comprising a distal end secured to the adapter and disposed within the adapter, wherein in response to the advancing the translation feature in the distal direction along the slot, the adapter is configured to slide distally within the housing and to lock to the distal end of the housing; and moving the translation feature in a proximal direction along the slot with the adapter locked to the distal end of the housing, wherein in response to the moving the translation feature in the proximal direction along the slot with the adapter locked to the distal end of the housing, the corrugated tube is configured to expand to shield the introducer needle within the corrugated tube and extends between the needle hub and the adapter.

14. The method of claim 13, wherein the adapter comprises the distal end and the proximal end, and the corrugated tube is compressed between the distal end of the adapter and the proximal end of the adapter.

15. The method of claim 13, wherein in response to the moving the translation feature in the proximal direction along the slot with the adapter locked to the distal end of the housing, the introducer needle is retracted within the housing.

16. A method for advancing and shielding an introducer needle, comprising:

advancing a translation feature in a distal direction along a slot of a housing of a vascular access device, the vascular access device comprising:

the housing comprising a proximal end, a distal end, and the slot extending longitudinally between the proximal end and the distal end;

a catheter assembly comprising a catheter hub and a catheter extending distally from the catheter hub, wherein at least a portion of the catheter assembly is disposed within the housing; and a needle assembly comprising a needle hub, the introducer needle extending distally from the needle hub through the catheter, and the translation feature coupled to the needle hub and configured to move longitudinally along the slot to translate the needle hub within the housing, wherein in response to advancing the translation feature in the distal direction along the slot, the introducer needle and the catheter are configured to advance beyond the distal end of the housing;

an adapter disposed in between the catheter hub and the needle hub, wherein the adapter comprises a distal end and a proximal end, wherein the proximal end of the adapter is fixed with respect to the distal end of the adapter; and a corrugated tube compressed within the adapter and comprising a distal end secured to the adapter and disposed within the adapter, wherein in response to the advancing the translation feature in the distal direction along the slot, the adapter is configured to slide distally within the housing and to lock to the distal end of the housing while the corrugated tube is compressed within the adapter; and moving the translation feature in a proximal direction along the slot with the adapter locked to the distal end of the housing, wherein in response to the moving the translation feature in the proximal direction along the slot with the adapter locked to the distal end of the housing, the corrugated tube is configured to expand to shield the introducer needle within the corrugated tube and extends between the needle hub and the adapter.

* * * * *